United States Patent [19]

Roubicek

[11] Patent Number: 5,248,613
[45] Date of Patent: Sep. 28, 1993

[54] NONHOMOGENEOUS CENTRIFUGAL FILM BIOREACTOR

[76] Inventor: Rudolf V. Roubicek, 1304 Delano, Las Cruces, N. Mex. 88001

[21] Appl. No.: 726,765

[22] Filed: Jul. 8, 1991

[51] Int. Cl.$^5$ ............................................. C12M 1/06
[52] U.S. Cl. ................................. 435/315; 210/219; 261/83; 261/84; 261/89; 422/224; 422/225; 422/227; 422/228; 435/313; 435/316
[58] Field of Search ..................... 435/284–287, 435/313–316; 210/219; 261/83, 84, 89; 422/227, 224, 225, 228, 229

[56] References Cited

U.S. PATENT DOCUMENTS

| | | | |
|---|---|---|---|
| 4,224,414 | 9/1980 | Vanderveen et al. | 435/315 |
| 4,287,137 | 9/1981 | Sonoyama et al. | 435/315 |
| 4,310,437 | 1/1982 | Schreiber | 435/315 |
| 4,519,959 | 5/1985 | Takeuchi et al. | 435/316 |
| 4,657,677 | 4/1987 | Roubicek et al. | 210/219 |
| 4,683,062 | 7/1987 | Krovak et al. | 435/299 |
| 4,717,669 | 1/1988 | Feres et al. | 435/315 |
| 4,782,024 | 11/1988 | Scott et al. | 435/313 |
| 4,893,935 | 1/1990 | Mandel et al. | 435/291 |
| 4,906,577 | 3/1990 | Armstrong et al. | 435/287 |
| 4,960,706 | 10/1990 | Bliem et al. | 435/284 |

*Primary Examiner*—Robert J. Warden
*Assistant Examiner*—Amalia Santiago
*Attorney, Agent, or Firm*—Milton D. Wyrick

[57] ABSTRACT

A centrifugal film bioreactor useful for processing both shear sensitive and shear requiring or tolerant cells. A liquid phase is directed upward in a guide tube to rotating truncated conical surfaces which transport the liquid phase across their surfaces. After leaving the conical surfaces, the liquid passes through a gaseous phase and may contact the wall of the fermentation vessel and then combine with the downward moving liquid phase in the lower part of the fermentation vessel, where it circulates. The maximum entrainment of the gaseous phase into the liquid phase occurs while the liquid phase is passing through the gaseous phase. Different configurations of guide tube propellers and fermentation vessel, allow for processing of different shear tolerant cells.

15 Claims, 5 Drawing Sheets

NONHOMOGENEOUS CENTRIFUGAL FILM BIOREACTOR

The present invention relates to the field of bioreactors for the cultivation of cells, and, more particularly to improved bioreactors utilizing rotating cones to cultivate both shear sensitive cells, as well as cells which are either shear resistant or require shear.

The most important factor in industrial aerobic processes is the efficient oxygen transfer into the liquid nutrient medium. Conventional equipment for the practice of such processes generally consists of a vessel equipped with means for introducing gases, such as oxygen, air, or carbon dioxide into the fermentation liquor and a motor-driven mechanical mixing means to provide intense agitation to facilitate this process.

This agitation, as practiced in prior art reactors, is carried out by powerful agitation means such as closed or open turbines which, in addition to creating a powerful turbulent flow of the fermented medium, produces great quantities of small bubbles of the supplied gaseous phase within the fermentation liquor. This process facilitates the molecular transport between the gaseous phase and the fermentation liquor, and provides both adequate flow and aeration of the liquid nutrient medium, which are necessary conditions for the cultivation of all aerobic microorganisms on an industrial scale.

The mass transfer capabilities of such equipment can be improved, for example, by such modifications as the use of baffling systems, draft tubes, or air lift tubes. However, each of these conventional methods requires a great deal of mechanical energy to distribute the gaseous phase through the liquid phase, and to provide the necessary mixing in large industrial scale equipment. These methods have presented both technical and economic problems, as well as creating high shear stresses on the cells from the mechanical agitation of the fermentation liquor in many conventional fermenters.

Another problem with conventional fermenters concerns the foaming produced by the mechanical agitation and aeration. In these fermenters, the introduction of large quantities of gas into the vigorously agitated fermentation liquor often produces great quantities of foam in the reaction vessel. This foaming has plagued aerobic processes for decades, as it severely limits the usable volume of the reaction vessel, and often can render the fermentation process microbially contaminated. All of these problems have a substantially adverse effect on the product yield and cost effectiveness of conventional fermentation processes.

Numerous attempts involving chemicals and mechanical devices have been heretofore proposed to solve the foaming problem in industrial biosynthesis processes. Most of these proposed solutions were intended to defoam after a foam had developed. The chemical treatments currently used for defoaming involve silicones and other water-immiscible additives which substantially decrease the rate of oxygen transfer, thereby interfering with the effectiveness of the process of aerobic biosynthesis. The mechanical methods of defoaming which are sometimes used in fermentation processes typically require an additional power source and a particular fermenter design to accomodate the defoaming equipment. These mechanical defoamers are neither always reliable nor feasible, particularly in large fermentation vessels.

In summary, the disadvantages of the prior art procedures for mass transfer in aerobic processes are the high energy costs associated with mixing and aeration, heavy foaming, high shear stress on cells, and all too frequent incidents of contamination in powerfully aerated systems. Each of these disadvantages interferes with the efficiency and economy of fermentation processes.

Fermentation equipment which, among other things, diminishes the foaming of the prior art and provides far more efficient fermenters are described in U.S. Pat. Nos. 4,657,677 (the '677 patent) and 4,717,669 (the '669 patent) to Roubicek and Feres.

The equipment disclosed in the '677 patent provides an improvement in mass transfer achieved by drawing a thin film of liquid upward along the surface of an inverted rotating truncated cone. This process continuously exposes a large area of liquid to a relatively static gaseous phase. This equipment is extremely useful in promoting efficient molecular transfer of gases, even those having low solubility in liquid. For example, the transport of oxygen from air into an aqueous phase, as occurs in conventional aerobic fermentation processes. Alternatively, the principle of this system can be employed for gas transfer in the reverse direction, as occurs in stripping, defoaming and deodorization. Another important feature of this equipment is the fact that the thin film process prevents the formation of foam, a serious problem with prior art fermentation processes. As previously stated, traditional prior art methods of foam control have necessarily been directed toward control of an existing foam, not toward preventing its formation.

In general, the invention disclosed in this patent can be characterized as having three regions of liquid flow and mass transfer. The first region is based on the liquid flow over the rotating surface. The second is the flow of droplets or liquid film through the stationary gaseous phase. The third region is characterized by a falling film created at the wall of the reactor. This system requires a minimal power input and thus it is suitable for cultivation only of shear sensitive cells. However, it is not suitable for mixing, liquid transport, or mass transfer of substrates requiring high shear.

The invention disclosed in the '699 patent is for a complete fermenter comprising a typical sterilizable fermentation vessel at the top of which a drive means is attached to a central shaft which is itself attached to a distributor. The distributor is open at its lower end and has fixedly attached to it one or more conical surfaces. Alternatively, the conical surfaces may be spaced apart from the distributor's lower end, and be driven by a separate drive means.

The substantial benefit of the invention disclosed in this patent is the vertical flow of the fermentation medium which is created by a propeller pump system consisting of a guide tube at the bottom of which an upflow-pitched propeller is rotating. If the guide tube is jacketed, it functions additionally as a heat exchanger. The pump also creates a head in the guide tube, and, if the rotating distributor has its lower end immersed into the liquid phase, the liquid is drawn upwardly along the inner surfaces of the distributor and, if ejected, through a set of openings onto the rotating conical surfaces. As this is happening, a flow of gas over the thin liquid film flowing across the conical surfaces is created by the same centrifugal force that is moving the liquid along the conical surfaces.

The flow of liquid to the distributor is controlled by varying the level of the liquid in the guide tube, or by adjusting the vertical position of the distributor. When desired, the gaseous phase can be supplied either at the bottom of the fermenter through a gas sparging system, or at the top of the fermenter. Alternatively, the gaseous phase can be introduced both at the bottom and the top. The invention, thus described, is known as a centrifugal film fermenter.

As stated, it is the axial propeller pump at the lower end of the guide tube which raises the liquid level to the distributor. In general the invention described in this patent can be characterized as employing a very large area of rotating surfaces to initiate an efficient mass transfer between the stationary and/or also moving gaseous phase and liquid film. In spite of the fact that a very efficient mass transfer is achieved by the equipment disclosed in this patent, the following two main disadvantages can be observed: first, pumping then distribution of the liquid, and finally the means to rotate a plurality of surfaces of large area, require a large amount of power and consequently create a condition of high shear which is not suitable for cultivation of shear sensitive cells; second, the system employing seven regions of liquid flow as described in the '669 patent is not suitable for cultivation of media of high viscosities and/or media of high densities containing suspended particles, primarily because of inconveniences based on the difficulties encountered in passing a liquid with this kind of rheology through all regions of the liquid flow, and particularly through the openings of the distributor. Clogging of the openings in the distributor will invalidate the process. Thus, even with the advances in fermenter design disclosed in the two patents discussed above, no prior art fermenter process is sufficiently versatile to satisfy the need for the alternative cultivation of both shear sensitive and shear dependent cells. Typically, the major components of the fermentation equipment for either the cultivation of shear sensitive cells, or the cultivation of shear dependent cells is extremely expensive, and not, at present, interchangeable between the two. Consequently, companies which are involved in both shear sensitive and shear dependent cell cultivation are required to make large investments in separate equipment for the cultivation of each class of cell.

Furthermore, experimental work in developing the present invention has shown that, in contrast with our '677 and '669 patents, the maximum mass transfer from the gaseous phase into the liquid phase occurs in the third region, where droplets or a thin film of the liquid phase leaves the top of the rotating surfaces and passes through the gaseous phase. As a matter of fact, this also substantially simplifies the process and the design, and enables the versatility of the centrifugal film bioreactor according to the present invention.

It is therefore an object of the present invention to provide fermenter apparatus which will allow the same fermenter to cultivate both shear sensitive and shear dependent cells.

It is another object of the present invention to provide fermenter apparatus which can be easily reconfigured to process a variety of liquid media.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention comprises a closed sterilizable fermentation vessel having a top section, a wall section and a bottom section. A liquid phase is in the bottom section of the fermentation vessel and a gaseous phase is introducible into the bottom section and/or into the top section of the fermentation vessel for mixing with the liquid phase. Guide tube means having an inner and outer surface are centrally disposed within the fermentation vessel for guiding the liquid phase from the bottom section of the fermentation vessel toward the top section of the fermentation vessel. One or more propeller means are disposed within the guide tube means for propelling the liquid phase upward through the guide means. One or more truncated conical surfaces are disposed in the top section of the fermentation vessel with the narrow ends of the one or more truncated conical surfaces extending into the guide tube means for transporting the liquid phase from the guide tube across the one or more truncated conical surfaces and through the gaseous phase into the liquid phase in the bottom section of the fermentation vessel. And one or more rotation means are connected by one or more shafts to the one or more propeller means and to the one or more truncated conical surfaces for rotating the one or more propeller means and the one or more truncated conical surfaces at predetermined rotational speeds. Wherein maximum entrainment of the gaseous phase into the liquid occurs as the liquid phase leaves the truncated conical surfaces and passes through the gaseous phase.

In a further aspect of the present invention, and in accordance with its objects and purposes, the apparatus of the invention comprises a closed sterilizable fermentation vessel having a top section, a wall section and a bottom section. A liquid phase is in the bottom section of the fermentation vessel, and a gaseous phase is introducible into the bottom section and/or the top section of the fermentation vessel for mixing with the liquid phase. Guide tube means having an inner and outer surface are centrally disposed within the fermentation vessel for guiding the liquid phase from the bottom section of the fermentation vessel toward the top section of the fermentation vessel. One or more propeller means are disposed within the guide tube means for propelling the liquid phase upward through the guide tube means. A cylindrical shell is disposed in the upper section of the fermentation vessel, the shell being open at its top and bottom ends and tapering inward toward its longitudinal axis to an opening at its bottom end. The shell has a plurality of openings in its side wall, and the tapered end of the shell extends into the guide tube means. A plurality of truncated conical surfaces is disposed inside the shell, the truncated conical surfaces having substantially identical half angles and different heights. The narrow ends of the plurality of truncated conical surfaces and the tapered end of the shell extend into the guide tube means for transporting the liquid phase from the guide tube across the plurality of truncated conical surfaces and through the gaseous phase to the liquid phase in the bottom of the fermentation vessel. And one or more rotation means are connected by one or more shafts to the one or more propeller means and to the shell for rotating the one or more propeller means and the shell at predetermined rotational speeds. Wherein maximum entrainment of the gaseous phase into the liquid occurs as the liquid phase leaves the openings in the shell and passes through the gaseous phase.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
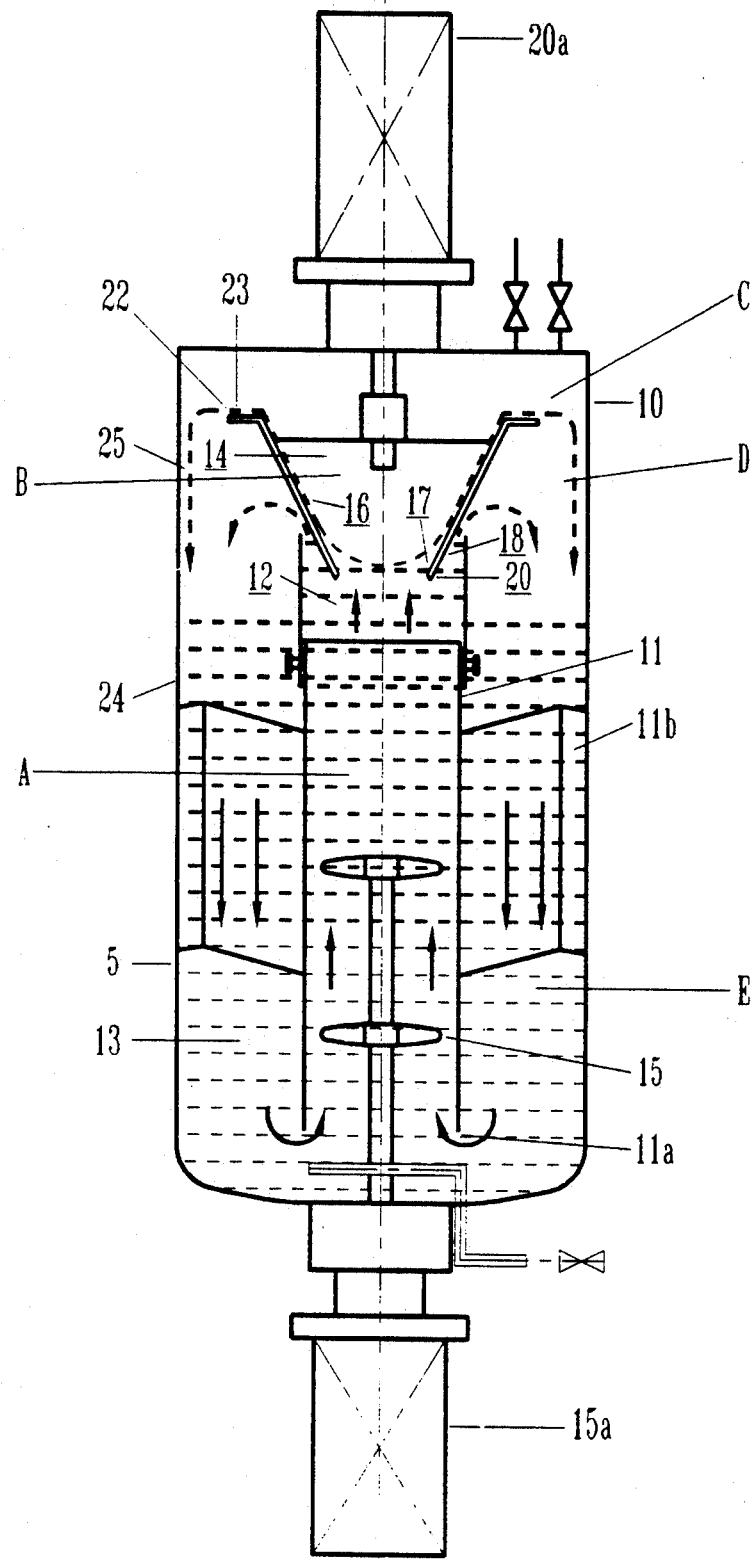
FIG. 1 is a longitudinal cross-section of one embodiment of the present invention which schematically illustrates five regions of the mass transfer and liquid flow in the bioreactor of the present invention.
Figure 2:
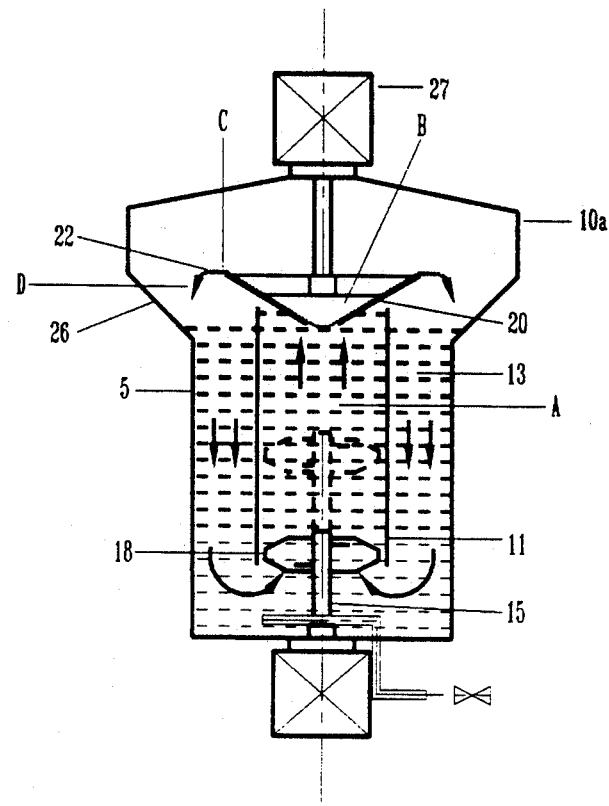
FIG. 2 is an embodiment of the present invention in which one or two (the second shown by dashed lines) mirror-polished propellers initiate a low shear flow toward a wide-angled rotating cone and a large diameter bioreactor head.
Figure 3:
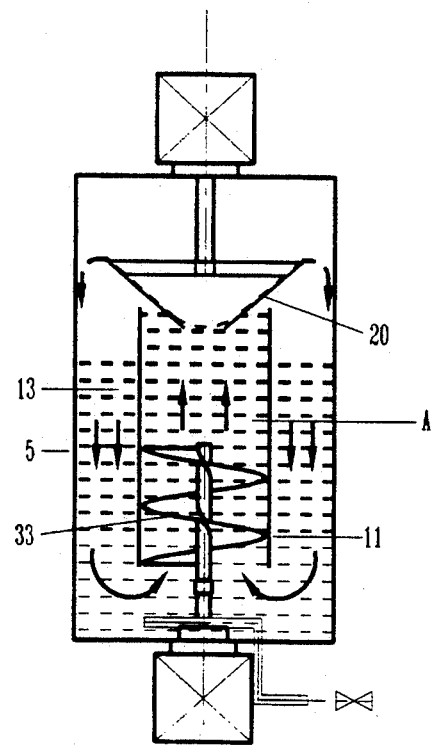
FIG. 3 is an embodiment of the present invention wherein a helical mixing impeller initiates the low shear flow toward a rotating cone.

The present invention provides a non-homogeneous fermenter having a great deal of versatility in handling a wide range of cell types, both those sensitive to shear and those with either a relative insensitivity to shear or with a growth rate which is shear dependent. This is accomplished by providing the guide tube with means for sustaining an axial flow in the upward direction, which means can be interchanged to allow a single centrifugal film fermenter to process cells of the above-mentioned types. The invention can be best understood by referring to the Figures, wherein cross-sectional views of centrifugal film fermenters are illustrated, each illustrating an aspect of the present invention. FIG. 1 describes the principles of this invention and illustrates the five regions of liquid flow and mass transfer of this non-homogenous bioreactor. FIGS. 2–3 illustrate bioreactors for cultivation of low shear stress cells. FIGS. 4–9 illustrate embodiments intended for cultivation of shear resistant or shear dependent cells.

FIG. 1 illustrates in cross-section the principles of operation of a non-homogenous bioreactor according to the present invention, in which mass transfer is carried out in five regions within bioreactor 5, these five regions being designated in FIG. 1 as regions A, B, C, D, and E. The first region of mass transfer, A, occurs in guide tube 11.

In this region, an axial liquid flow is established, creating head 12 in guide tube 11 which is the initial area for liquid flow and mass transfer. Simultaneously, air or oxygen or a mixture of the two, or any desired gas is supplied at bottom 11a of guide tube 11 beneath mixing and pumping device 15. It is the function of mixing and pumping device 15 to provide upward movement to liquid phase 13, and to provide mixing of liquid phase 13 and whatever gas might be supplied at bottom 11a.

Guide tube 11 is disposed centrally within fermentation vessel 10, and is maintained in position by wings 11b. Wings 11b may be bolted to flanges (not shown) attached to fermentation vessel wall 24, or simply pressure fit to fermentation vessel 10. The pressure fit could be accomplished by bending the ends of wings 11b at an angle so that the ends would be substantially parallel to fermentation vessel wall 24.

In addition to providing axial flow to liquid phase 13, a primary purpose of guide tube 11 is to supply oxygen and/or air into regions B, C, and D, where additional rapid mass transfer occurs by diffusion. In general, a much lower gas or air rate of flow is required by this invention than is required by prior art processes.

In region B, three actions take place: first, oxygen transfer from the relatively stationary gaseous phase 14 into a thin liquid film 16 which is created on the inner side 17 and outer side 18 of conical surface or truncated cone 20 by the action of centrifugal, gravitational, and Coriolis forces. The second action is an efficient pumping effect initiated by vertically immersing the narrow end of conical surface 20 into the upward flowing liquid phase 13 in guide tube 11. In the third action, which occurs at the same time, gaseous bubbles are removed from liquid phase 13 due to centrifugal force, thus preventing foaming of liquid phase 13.

However, the most efficient mass transfer occurs in region C. The characteristic feature of this region is the formation of droplets 22 which are formed at the point where liquid phase 13 leaves flange 23 of conical surface 20. An intensive flow of droplets 22 can be observed with liquid phase 13 of a low viscosity, and a thin liquid film (not shown) for liquid phase 13 of a high viscosity.

Mass transfer occurs by diffusion between the relatively fast moving droplets 22 or thin liquid film and the relatively stationary gaseous phase 14. The mass transfer rate is dependent on the size and geometry of liquid droplets 22 or the thickness of the thin liquid film, the distance of flange 23 from fermenter wall 24, the trajectory of liquid droplets 22 or the thin liquid film, and the impact of the liquid droplets 22 or the thin liquid film on fermenter wall 24.

In region D of FIG. 1, a falling film 25 is formed, and mass transfer between the falling liquid film 25 and relatively stationary gaseous phase 14 occurs. The fifth and last region, region E, can be characterized as a bulk liquid phase 13, containing well dispersed, very small bubbles inside the bulk of liquid phase 13 which is moving down toward the bottom of bioreactor 10. The well distributed small bubbles enable a high rate of oxygen transfer. This action is enhanced by wings 11b, which function as baffles directing the flow of liquid phase 13 in the downward direction.

A special feature of the present embodiment is the observation that, at higher rotational speeds of mixing and pumping device 15, a vortex forms at the top of guide tube 11. When the narrower end of conical surface 20 is immersed into this vortex, a self-propelling rotation of conical surfaces 20 occurs even without supplying rotational power from upper rotation means 20a. Conversely, a flow across conical surface 20 can be maintained with conical surface 20 rotating, but with mixing and pumping device 15 and its lower rotation means 15a motionless. Upper rotation means 20a and lower rotation means 15a may be any properly rated electric motors connected to conical surface 20 and mixing and pumping device 15 by conventional separate shafts.

FIGS. 2 and 3 show arrangements used for cultivation of shear sensitive microorganisms. This arrangement is characterized by using inside guide tube 11 (region A of FIG. 1) means for initiating low shear flow of liquid phase 13 in the upward direction and employing conical surfaces 20. Although the half angles of conical surfaces 20 are not accurately depicted in FIGS. 2 and 3, conical surfaces 20 should have half angles of greater than 37 degrees.

Referring now to FIG. 2, wherein there is illustrated an arrangement of flow of liquid phase 13 and mass transfer as was described for FIG. 1. It consists of the same means of axial flow in guide tube 11, that is with mixing and pumping device 15 of FIG. 1 being mirror polished propeller 18, although a second propeller (or more), shown in dashed lines can also be employed. In this configuration, mixing and pumping device 15 is operating at a low rotational speed. Also, conical surface 20, having, a half angle greater than 37 degrees, and immersed into the head of liquid phase 13, rotates at a low rotational speed. The difference in FIG. 2 is the enlarged diameter of upper portion 10a of bioreactor 5, which prohibits or lessens the effect of collision of droplets 22 with wall 26 of bioreactor 5.

In the arrangement where a pair or more of propellers 18 are employed, a very low rotational speed of propellers 18, that is, a speed less than 300 rpm, will produce a low shear axial flow in guide tube 11. Alternatively, the axial flow in guide tube 11 can be initiated only through the action of conical surface 20 with upper drive means 27, without rotating propellers 18.

Reference should now be directed to FIG. 3, where a bioreactor 5 similar to that shown in FIG. 1 is illustrated. The primary difference between the embodiment of FIG. 1 and the embodiment of FIG. 3 is helical impeller 33. This embodiment is most useful when sensitive cells are cultivated in a viscous liquid phase 13 or in a liquid phase 13 having a high density which is axially transported through guide tube 11.

FIGS. 4–9 illustrate the objectives of the present invention which consist of employing different combinations of apparatus which initiate the turbulent and high-shear flow and aeration to create a high rate of oxygen transfer during the cultivation of the shear-resistant or tolerant microorganisms and/or the production of metabolites thereof.

To achieve the turbulent, and thus a high shear flow of liquid phase 13, powerful means of liquid flow in the axial and upward direction in guide tube 11 are used preferably in combination with baffles inside guide tube 11 and/or conical surfaces 20 having half angles of 37 degrees or less. The arrangements for the cultivation of shear sensitive cells illustrated in FIGS. 2 and 3, and for shear requiring cells illustrated in FIGS. 4–9, differ from the conventional fermenters and from the above described centrifugal film fermenters by employing five regions of liquid flow and mass transfer, interchangeability of mixing and pumping devices 15 (FIG. 1) for initiating liquid flow of low and high shear thus providing versatility and economy for the production of metabolites.

Figure 4:
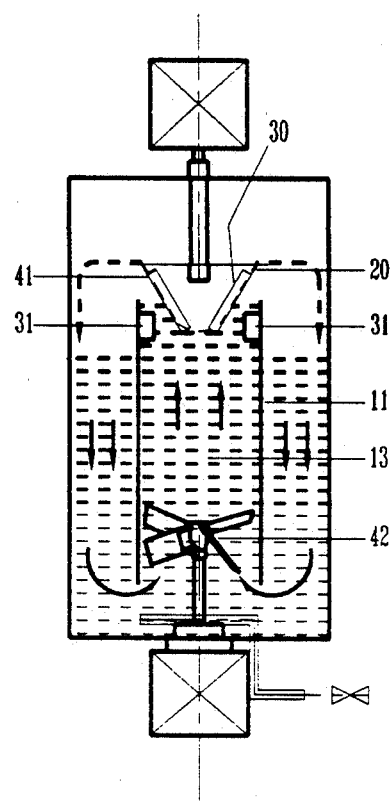
FIG. 4 is an embodiment of the present invention in which a pitched four-blade impeller initiates a high-stress axial flow of media in a baffled guide tube and into a baffled narrow-angled rotating cone.

FIG. 4 shows four-blade impeller arrangement 42 for forming a powerful upward flow in guide tube 11.. Also shown is a conical surface 41 Although the half angle of conical surface 41 is not accurately depicted in FIG. 4, conical surface 41 should have a half angle of 37 degrees or less. Attached to conical surface 41 are several baffles or blade means 30 pitched at an angle to the surface of conical surface 20 sufficient to provide an upward flow along conical surface 20. The application of baffles 30 is optional. These features initiate a powerful liquid flow over conical surface 20. To inhibit the formation of a vortex at the top of guide tube 11, the inner wall of guide tube 11 also has baffles 31 attached.

Figure 5:
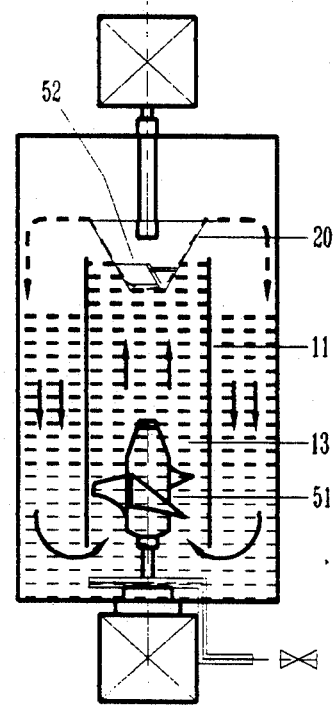
FIG. 5 is an embodiment of the present invention in which a foil impeller and a baffled narrow-angled rotating cone create a turbulent liquid flow throughout the reactor.

FIG. 5 shows an embodiment similar to that shown in FIG. 4 except that a foil impeller 51 is used to initiate a powerful flow of liquid phase 13 in guide tube 11. Also, short, pitched baffles 52 can be fixed to the inner surface of conical surface 20 to produce a powerful flow of liquid phase 13 over conical surface 20.

Figure 6:
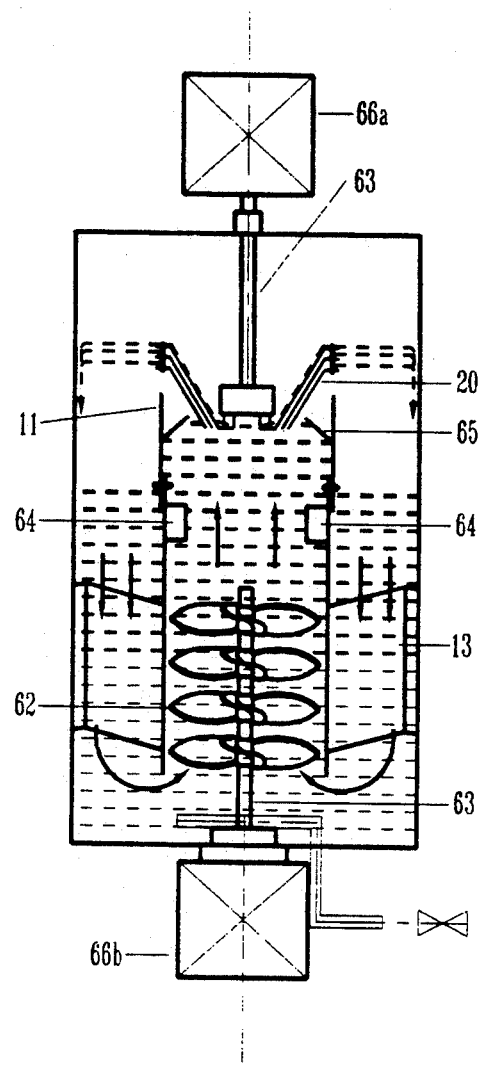
FIG. 6 is a plan view of a reactor utilizing multiple propellers in the guide tube and a slanted circumferential baffle at the top of the guide tube and a system of rotating conical surfaces vertically attached to a common shaft.
Figure 7:
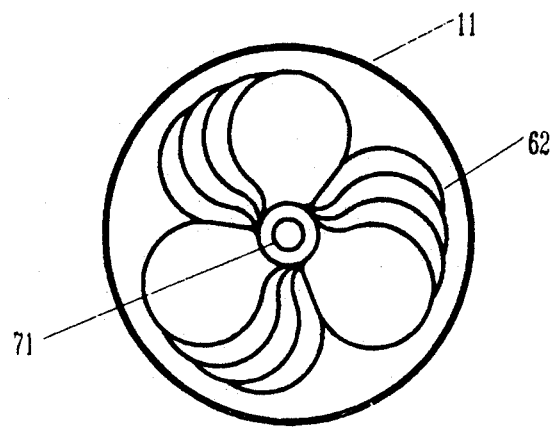
FIG. 7 is a top view of a multiple propeller arrangement which can have the distance between individual propellers, and the angle of the propellers adjusted for different flow rates.

Another embodiment of the present invention is illustrated in FIGS. 6 and 7. In FIG. 6, a cross-section similar to those of the other Figures is illustrated except for the provision of multiple conical surfaces 20 and multiple propellers 62 mounted to shaft 63, the former to the upper portion of shaft 63 and the latter to the lower portion of shaft 63. Alternatively, conical surfaces 20 can be attached by a shaft to upper drive means 66a and multiple propellers 62 can be attached to a separated shaft (not shown) and driven by bottom driving means 66b.

The vertical distance between individual propellers 62 is adjustable to achieve a desired flow rate of liquid phase 13 within guide tube 11. Vertical baffles 64 fixed to guide tube 11 inhibit formation of a vortex of liquid medium 13 at the top of guide tube 11. Slanted circumferential baffle 65 fixed near the top of guide tube 11 also can be used to direct liquid phase 13 into multiple conical surfaces 20. This design of multiple propeller 62 enhances the flow of a very viscous liquid phase 13 which otherwise would not be possible to transport axially through guide tube 11.

In FIG. 7, multiple propellers 62 of FIG. 6 are illustrated in a top view which shows multiple pitched propellers mounted on common shaft 71. In this view, each propeller of multiple propellers 62 is at an angle of 15 degrees with respect to its next previous propeller, although they may be at any desired angle. Shifting individual propellers at an angle causes multiple propellers 62 to act as a screw conveyor applicable even for transport of liquid phase 13 (FIG. 6) having viscosities over 40,000 centipoises. Handling liquid phase 13 having such viscosities with any prior art equipment would be impossible.

Figure 8:
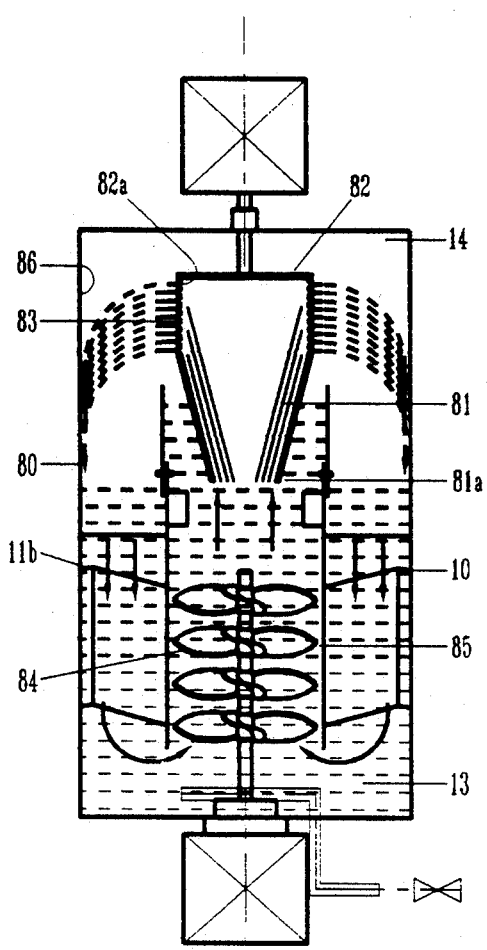
FIG. 8 is a plan view of a set of cones fixed inside a shell which is provided with openings to direct the liquid flow through gaseous phase at the top of the fermenter.
Figure 9:
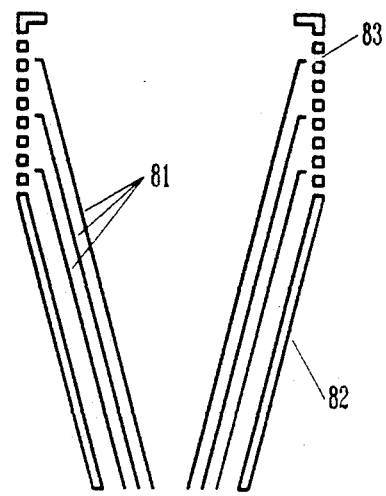
FIG. 9 is a plan view of the arrangement of cones in the shell illustrated in FIG. 8.

FIGS. 8 and 9 illustrate another embodiment of the present invention for the cultivation of high shear tolerant cells. FIG. 8 shows a set of flanged conical surfaces 81 having graduated heights inside shell 82. Shell 82 is equipped with openings 83 which may be either small or large orifices of slots, depending on the rheological characteristics of liquid phase 13.

Similar to the operation of the above described embodiments, the operation this embodiment involves immersing narrow ends 81a of flanged conical surfaces 81, including shell 82, into liquid phase which has been raised by the action of propeller pump 84 inside guide tube 85. The forceful flow of liquid phase 13 is initiated by centrifugal forces, and liquid phase 13 is collected in the space between flanged conical surfaces 81 and inner surface 82a of shell 82. In particular, the gravitational force creates a considerable pressure at surface 82a of shell 82, forcing liquid phase 13 to flow under conditions of high shear through openings 83 toward wall 86 of fermenter 80, thus substantially enhancing the area of contact between the fast moving liquid phase 13 in several layers, depending on the number of flanged conical surfaces employed, and the relatively stationary gaseous phase 14.

FIG. 9 illustrated the detail of the configuration of flanged conical surfaces 81, inside shell 82, and openings 83 in shell 82. Particular attention should be paid to the arrangement of openings 83. The diameter of openings 83, which can be circular orifices or slots, can be of variable dimensions, depending on the viscosity or density of a particular liquid phase 13 (FIG. 8). Openings 83 can easily be made adjustable so that they can handle a wide range of viscosities and densities of liquid phase 13.

It will be clear to those skilled in the art that any of the propeller arrangements illustrated for either shear sensitive or shear resistant can be easily interchanged. For example, individual propellers can be fitted to a grooved shaft and bolted to it. Access is gained through removable flanges at the bottom of bioreactor 5 (FIG. 1).

A surprising result of using the embodiment illustrated in FIGS. 6 and 7 was discovered when using multiple propellers 62 without any multiple conical surfaces 20 in place. In this configuration, it was verified that, when aerated, excellent mass transfer was obtained even without multiple conical surfaces 20. This was due to the powerful axial flow of liquid phase 13 flowing out of guide tube 11. The mass transfer was superior to that obtained with conventional fermenters, such as the Rushton turbines, but inferior to that obtained with use of multiple conical surfaces 20.

Testing has indicated the present invention is far superior even to the rotating cone technology disclosed in my two prior patents, the '677 patent, and the '669 patent. This testing indicated that with the embodiments disclosed herein the main mass transfer occurs not on conical surfaces 20, but when liquid phase 13 leaves conical surfaces 20 and passes as droplets of a liquid film through gaseous phase 14 to the bottom of bioreactor 10. As an illustration, the value of the volumetric oxygen transfer coefficient ($K_La$) was found to be 190 hr$^{-1}$ with the present invention, 105 hr$^{-1}$ for the arrangement according to the '669 patent, and 15 hr$^{-1}$ for the arrangement according to the '677 patent.

Although the figures, for example as shown in FIG. 1, have illustrated separate upper rotation means 20a and lower rotation means 15a, it will be clear to those skilled in the art that a single rotation means can be connected to both conical surfaces 20 and mixing and pumping device 15. A single, common shaft could connect a single rotation means to conical surfaces 20 and to mixing and pumping device 15.

The foregoing description of embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A centrifugal film bioreactior, comprising:
   a sterilizable fermentation vessel having a top section and a bottom section, and a wall section interposed between said top section and said bottom section;
   means for introducing a liquid phase into said bottom section and said wall section of said fermentation vessel;
   means for introducing a gaseous phase into one of said bottom section or said top section of said fermentation vessel for contacting with said liquid phase;
   guide tube means having an inner and outer surface centrally disposed within said fermentation vessel for guiding said liquid phase from said bottom section of said fermentation vessel toward said top section of said fermentation vessel;
   one or more propeller means disposed within said guide tube means for propelling said liquid phase upward through said guide tube means;
   one or more truncated cones, each having two opposing ends, one end being narrower than the other end, each of said cones further having inside and outside surfaces and each of said cones being disposed in said top section of said fermentation vessel with said narrower ends of said one or more truncated cones extending into said guide tube means for transporting said liquid phase from said guide tube means across said one or more truncated cones and through said gaseous phase into said liquid phase in said wall section and said bottom section of said fermentation vessel; and
   blade means fixed to said inside surfaces of said truncated cones near said narrower ends, said blade means being pitched at a predetermined angle to said inside surface, for directing an upward flow of said liquid phase along said inside surface;
   one or more rotation means respectively connected by respective one or more shafts to said one or more propeller means and to said one or more truncated cones for rotating said one or more propeller means and said one or more truncated cones at predetermined rotational speeds;
   wherein maximum contact of said gaseous phase with said liquid phase occurs as said liquid phase leaves said truncated cones and passes through said gaseous phase.

2. The apparatus as described in claim 1, wherein said one or more rotation means comprises one rotation means connected by a single shaft to both of said one or more propeller means and to said one or more truncated cones.

3. The apparatus as described in claim 1, wherein said one or more rotation means comprises first and second rotation means, said first rotation means being connected by a first shaft to said one or more propeller means and said second rotation means being connected by a second shaft to said one or more truncated cones.

4. The apparatus as described in claim 1, wherein baffles which extend radially inward are fixed to said inner surface of said guide tube means for inhibiting formation of a vortex.

5. The apparatus as described in claim 1, wherein said top section of said fermentation vessel has a larger diameter than said bottom section of said fermentation vessel for providing additional contact time between said liquid phase leaving said conical surfaces and said gaseous phase.

6. The apparatus as described in claim 1, wherein said one or more propeller means comprises two propellers each containing two or more blades.

7. The apparatus as described in claim 1, wherein said one or more propeller means comprises a helical impeller.

8. The apparatus as described in claim 1, wherein said one or more propeller means comprises two or more propellers, individual blades of each propeller propeller defining a predetermined angle with respect to individual blades of its next previous propeller.

9. The apparatus as described in claim 1, wherein said one or more propeller means comprises one four-blade impeller.

10. A centrifugal film bioreactor, comprising:
a sterilizable fermentation vessel having a top section and a bottom section, and a wall section interposed between said top section and said bottom section;
means for introducing a liquid phase in said bottom section and said wall section of said fermentation vessel;
means for introducing a gaseous phase into one of said bottom section or said top section of said fermentation vessel for contacting with said liquid phase;
guide tube means having an inner and outer surface centrally disposed within said fermentation vessel for guiding said liquid phase from said bottom section of said fermentation vessel toward said top section of said fermentation vessel;
one or more propeller means disposed within said guide tube means for propelling said liquid phase upward through said guide tube means;
a generally cylindrical shell, disposed in said upper section of said fermentation vessel, said shell having two opposing ends and a sidewall and being opened at each of said two opposing ends and tapering inward toward its longitudinal axis near one end, and having a plurality of openings in its side wall;
a plurality of truncated cones each having two opposing ends, one end being narrower than the other end, each of said cones further having inside and outside surfaces and each of said truncated cones being disposed and attached inside said shell, said truncated cones having substantially identical half angles and different heights, with said narrower ends of said plurality of truncated cones and said tapered end of said shell extending into said guide tube means for transporting said liquid phase from said guide tube means across said plurality of truncated conical surfaces and through said openings into said gaseous phase, and therefrom into said liquid phase in said bottom section of said fermentation vessel; and
one or more rotation means respectively connected by respective one or more shafts to said one or more propeller means and to said shell for rotating said one or more propeller means and said shell at predetermined rotational speeds;
wherein maximum entrainment of said gaseous phase into said liquid occurs as said liquid phase leaves said openings in said shell and passes through said gaseous phase.

11. The apparatus as described in claim 10, wherein baffles which extend radially inward are fixed to said inner surface of said guide tube means for inhibiting formation of a vortex.

12. The apparatus as described in claim 10, wherein said top section of said fermentation vessel has a larger diameter than said bottom section of said fermentation vessel.

13. The apparatus as described in claim 10, wherein said one or more propeller means comprises two propellers each containing two or more blades.

14. The apparatus as described in claim 10, wherein said truncated cones have blades fixed to said inside surfaces of said truncated cones near said narrow ends, said blades being pitched at a predetermined angle to said inside surfaces, for directing an upward flow of said liquid phase along said inside surfaces.

15. The apparatus as described in claim 10, wherein said one or more propeller means comprises one four-blade impeller.

* * * * *